United States Patent [19]

Klein et al.

[11] Patent Number: 5,108,466
[45] Date of Patent: Apr. 28, 1992

[54] APPARATUS AND METHODS FOR CONTROLLING FLUIDS PROVIDED TO A CHROMATOGRAPHIC DETECTOR

[75] Inventors: Kenneth J. Klein, Wilmington, Del.; Robert C. Henderson, Avondale, Pa.; Richard J. Phillips, Landenberg, Pa.; Michael Q. Thompson, Coatesville, Pa.

[73] Assignee: Hewlett-Packard Company, Palo Alto, Calif.

[21] Appl. No.: 632,330

[22] Filed: Dec. 21, 1990

[51] Int. Cl.⁵ ............................................. B01D 15/08
[52] U.S. Cl. .................................... 55/20; 55/18; 55/21; 55/67; 55/197; 55/386
[58] Field of Search .............. 55/18, 20, 21, 67, 197, 55/208, 386, 210, 270

[56] References Cited

U.S. PATENT DOCUMENTS

| | | | |
|---|---|---|---|
| 3,250,057 | 5/1966 | Clarke | 55/67 |
| 3,345,804 | 10/1967 | Mariani et al. | 55/67 |
| 3,557,532 | 1/1971 | Broerman | 55/67 |
| 3,881,892 | 5/1975 | Gehrke et al. | 55/67 |
| 4,650,499 | 3/1987 | Scott | 55/18 |
| 4,871,453 | 10/1989 | Kumar | 55/386 X |
| 4,883,504 | 11/1989 | Gerstel | 55/67 |
| 4,948,389 | 8/1990 | Klein et al. | 55/20 |
| 4,976,750 | 12/1990 | Munari | 55/21 |
| 4,994,096 | 2/1991 | Klein et al. | 55/21 X |
| 4,999,162 | 3/1991 | Wells et al. | 55/386 X |

Primary Examiner—Robert Spitzer

[57] ABSTRACT

Apparatus and method are provided for controlling at least one physicochemical property of carrier fluids and/or support fluids provided to chromatographic detectors by determining a physicochemical property of the one or both fluids and controlling that property using interactive feedback loops.

24 Claims, 5 Drawing Sheets

APPARATUS AND METHODS FOR CONTROLLING FLUIDS PROVIDED TO A CHROMATOGRAPHIC DETECTOR

FIELD OF THE INVENTION

The present invention relates to an advancement in the art of chromatography and, more particularly, to an apparatus and method for effecting greater control over the fluids provided to a chromatographic detector.

BACKGROUND OF THE INVENTION

In analytical chemistry, liquid chromatography (LC) and gas chromatography (GC) techniques have become important tools in the identification of chemical sample components. The basic principle underlying all chromatographic techniques is the separation of a sample chemical mixture into individual components by transporting the mixture in a carrier fluid through a porous retentive media. The carrier fluid is referred to as the mobile phase and the retentive media is referred to as the stationary phase. The principal difference between liquid and gas chromatography is that the mobile phase is either a liquid or a gas, respectively.

In a GC apparatus, an inert carrier gas typically is passed through a temperature-controlled column which contains a stationary phase in the form of porous sorptive media. Gas chromatography columns have also been known to comprise a hollow capillary tube having an inner diameter in the range of few hundred microns coated with the stationary phase. A sample of the subject mixture is injected into the carrier gas stream and passed through the column. As the subject mixture passes through the column, it separates into its various components. Separation is due primarily to differences in the partial pressures of each sample component in the stationary phase versus the mobile phase. These differences are a function of the temperature within the column. A detector, positioned at the outlet end of the column, detects each of the separated components contained in the carrier fluid as they exit the column.

The analytical choice between liquid and gas chromatography techniques is largely dependent on the molecular weight of the components to be analyzed. Liquid chromatography devices are capable of analyzing much heavier compounds than gas chromatography devices. However, gas chromatography detection techniques are more sensitive and therefore are generally preferred.

The advent of supercritical fluid chromatography (SFC) provided a potential bridge between gas and liquid chromatography by providing relatively high sensitivity for higher molecular weight samples. In SFC, a fluid heated above its critical point is used as the mobile phase. This fluid is passed under pressure through a media which differentially retains sample components. As the pressure of the mobile phase is increased, for example, from about 40 atmospheres to approximately 400 atmospheres, the sample being analyzed separates into its various components in relation to the relative differential solubility of each component in the mobile phase. Since the mobile phase is a gas, the same detectors used in GC techniques can be utilized, significantly enhancing detector sensitivity and selectivity.

SFC has been found to be primarily useful in the analysis of compounds having molecular weights in the range of about 100 to about 10,000 and in the analysis of thermally labile molecules such as pesticides and pharmaceuticals. The problem with SFC, however, is that a considerable amount of time is required to conduct a sample analysis.

One approach to improved chromatographic devices has focused on programmed computer control. It is known, for example, to program the column temperature of a GC device. Since separation of the sample components is due primarily to differences in their partial pressures in the stationary phase versus the mobile phase and since these differences are a function of the temperature within the column, raising the column temperature either in a constant linear fashion or in a stepwise linear fashion over a sufficient range of temperature can assure high resolution of each sample component in a minimized time period.

It is also known that the time required for a temperature programmed GC analysis can be reduced even further by programming the flow rate of the carrier gas. Scott, R. P. W., "New Horizons in Column Performance", *Gas Chromatography*, 1964, 32-37 indicates that analysis time can be reduced by increasing the flow rate. However, while increasing the flow rate may reduce analysis time, efficiency and resolution are also reduced. This reduction may be accepted for analytes that have excess resolution on the column. This is similar to increasing the column temperature, which may not be possible for particularly labile analytes or stationary phases.

Costa Neto, C., et al., *Journal of Chromatography*, 1964, 15, 301-313 discusses programming the flow of the GC mobile phase in isothermic or temperature programmed runs in order to obtain the separation of complex mixtures. Costa Neto, et al. discuss the theoretical derivation of equations which relate flow rate to various chromatogram properties such as peak migration, peak width, peak area and peak height. Certain derivations also relate flow rate to efficiency and resolution. The programmed flow actually used by the authors was said to be manual in nature using a step valve.

Zlatkis, A., *Journal of Gas Chromatography*, March 1965, 75-81 discusses the use of a pneumatic flow controller for regulating flow rate in an exponential fashion between preset limits. In reviewing previous flow programming reports, such as the Costa Neto, et al. reference discussed above, Zlatkis et al. characterize that reference as discussing flow programming only in relation to so-called preparative gas chromatography, not practical analytical gas chromatography.

Nygren, S. et al., *Journal of Chromatography*, 1976, 123, 101-108 discuss flow programming through the use of a metering valve in the side outlet of an inlet splitter. Nygren, et al. state that results comparable to temperature programming could be achieved under certain circumstances by exponentially programming carrier gas flow.

More recently, Larson, J. R. et al., *Journal of Chromatography*; 1987, 405, 163-168 discuss a continuous flow programming technique for process capillary gas chromatography. However, these techniques do not have temperature programming capabilities. The authors concluded that by programming carrier gas flow in a process GC application, shorter cycle times could be achieved than with temperature programmed GC devices.

One problem with each of the flow programming devices discussed above is that carrier gas flow and/or column temperature systems operate independently of one another. In general, such independently operated closed loop systems are incapable of detecting undesirable conditions affecting the accuracy of the chromatographic analysis or of optimizing flow and temperature conditions simultaneously. Moreover, the systems are incapable of making adjustments to maintain multiple parameters at optimized conditions.

Thus, the invention disclosed by U.S. patent application Ser. No. 349,740, now U.S. Pat. No. 4,994,096, in the names of Klein, et al. represented a significant advance in the programming of chromatographic flow. Application Ser. No. 349,740, now U.S. Pat. No. 4,994,096 which is incorporated herein by reference, disclosed an open loop system for controlling the flow rate of a carrier fluid in a system wherein a portion of the chromatographic column is subjected to a temperature profile. By this open loop system, Klein, et al. overcame many of the problems of prior temperature and flow programming devices and also extended the molecular weight range of compounds capable of GC analysis.

However, the flow and temperature programming disclosed in application Ser. No. 349,740, now U.S. Pat. No. 4,994,096, is primarily directed toward effective compound chromatographic resolution. Neither that application nor the prior art focus on improving the detection of the resolved components. In fact, due to manner in which the flow rate of carrier fluids exiting a temperature-programmed column will vary over time, such fluids are not well suited for introduction into many of the flow-sensitive or pressure-sensitive chromatographic detectors commonly employed in the art. Variations in the flow rates or pressures of carrier fluids introduced into such detectors frequently will result in variability and non-optimization of detector response. There thus exists a need for a chromatographic device wherein the flow rate of the carrier fluid entering the chromatographic detector is carefully controlled to provide optimal detector response.

In addition, many of the commonly-employed chromatographic detectors require the provision of one or more support fluids. For example, the operation of detectors such as the flame photometric detector depends intimately upon the composition, pressure, and/or flow rate of several flame support fluids. Detector response attributes such as sensitivity, specificity, linear dynamic range, stability, and noninterference are also known to be dependent upon each support fluid and its physicochemical properties. However, none of the chromatographic devices presently known in the art are able to assure controlled provision of these support fluids. By carefully controlling the provision of detector support fluids, it may be possible to optimize one or more of the detector response attributes over the course of a chromatographic run.

SUMMARY OF THE INVENTION

The present invention provides apparatus and methods for controlling a chromatographic detector through careful control of the carrier fluids and/or support fluids provided thereto.

Apparatus for controlling the provision of carrier fluids preferably comprise means for determining the flow rate of the carrier fluid at a point upstream from the detector; means for generating a control signal in relation to the flow rate of the carrier fluid; and means for providing an amount of make-up fluid to the chromatographic system at a point between the column and the detector in relation to the control signal such that the carrier fluid passes to the detector at a predetermined flow rate.

Apparatus for controlling the provision of support fluids preferably comprise means for identifying at least one detector response attribute selected from the group consisting of sensitivity, selectivity, linear dynamic range, noninterference, activation, and robustness; means for determining at least one physicochemical property of the support fluid selected from the group consisting of composition, pressure, flow rate, viscosity, temperature, density, electronegativity, flammability, thermal conductivity, molecular weight, spectral emissions, and specific heat; processing means for generating a control signal in relation to a data set which comprises the detector response attribute and the physicochemical property; and means for modifying the physicochemical property in relation to the control signal.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

The apparatus and methods of the present invention may be employed to control a wide variety of fluids provided to chromatographic detectors. Fluids include gases, liquids, supercritical fluids, plastic solids, multiple component gases and liquids, and mixtures thereof capable of flow. Gases are preferred fluids according to the present invention.

Figure 1:
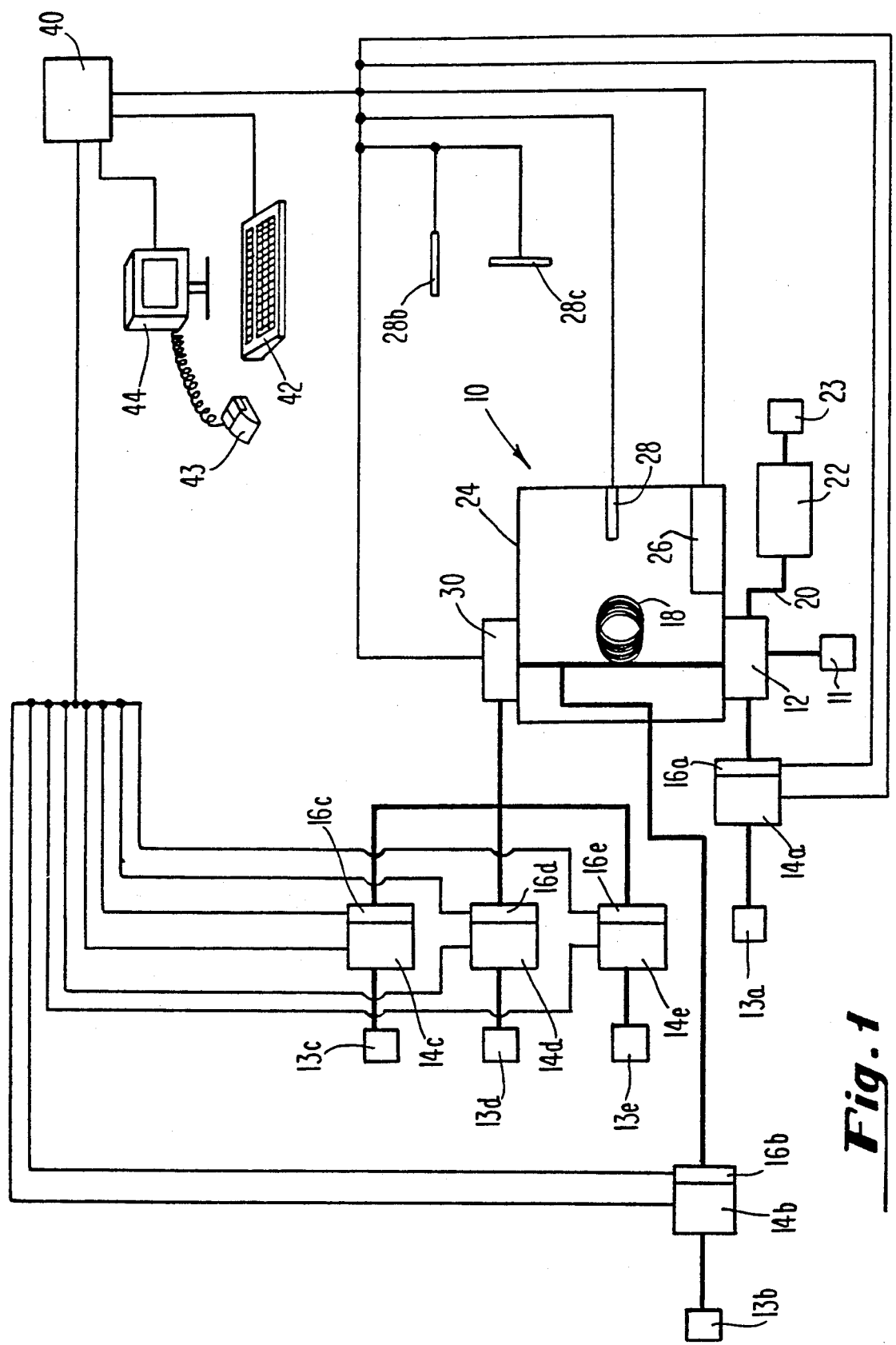
FIG. 1 is a block diagram of a forward pressure regulated gas chromatographic apparatus according to the present invention.

A gas chromatographic apparatus according to the present invention is shown in FIG. 1. The chromatograph (10) is arranged in a forward pressure regulated design suitable for direct, that is, non-split, injections. For example, this flow circuit typically would be used with so-called cool on-column, packed, and large bore (i.e., about 530 micron) direct techniques. In order to perform a chromatographic separation of a given sample compound, the sample (11) is injected into a pressurized carrier gas by means of an injection port (12). The carrier gas supplied to the injection port (12) is first provided from a source (13a) to a valve (14a). It will be appreciated that the carrier gas may comprise one or more component gasses—such as, for example, hydrogen, nitrogen, or helium—depending upon the particular chromatographic separation to be performed. A mixture of argon and 4% methane is common carrier gas used with electron capture detectors. It will be appreciated by those skilled in the art that opening or closing the valve (14a) serves to control both the pressure and the flow rate of the carrier gas in the GC system.

A transducer (16a) generates an electronic signal in relation to either the pressure or the flow rate of the carrier gas provided to the injection port (12). Preferably, a pressure signal is provided to a processing means (40), which in turn provides a control signal to the valve (14a). The valve (14a) then regulates the pressure of the carrier gas in response to a control signal. Although the particular design of valves (14a–e) is not critical to the present invention, a Model Number 001-1014 pressure valve sold by Porter Instrument Company, Inc. of Hatfield, Pennsylvania is preferred. In preferred embodiments, the transducers (16a–e) are 1210-A100G3L transducers sold by I.C. Sensors of Milpitas, CA. Generally, these pressure transducers will not need calibration, as their linear specifications are as good or better than most pressure calibration systems. It will be recognized, however, that the so-called zero offset will need to be corrected by any of the known methods.

The injection port (12) provides a portion of the carrier gas/sample combination to a column (18), with the remainder passing through a non-analyzed output (20). The flow exiting the output is known as the septum purge flow. By maintaining a relatively constant purge flow through a downstream-referenced mass flow controller (22), it is possible to minimize "false" peaks from the injection port septum (not shown) and also minimize air diffusion into the column (18). A purge flow of from about 2–4 milliliters per minute is preferred for packed, capillary split, or capillary splitless columns, 5–15 milliliters per minute for cool on-columns.

By incorporating the mass flow controller (22), a greater flow of carrier gas can be utilized. This, in turn, allows the valve (14a) to be operated in a region of greater control. For example, instead of using the valve (14a) to control the flow of carrier gas in the region of approximately less than one milliliter per minute for high resolution capillary column analyzers, the valve (14a) can instead be operated in a range of approximately 3–6 milliliters per minute minimum while still providing the same amount of the carrier gas/sample combination to the column (18). As shown in FIG. 1, the column (18) is positioned within an oven (24). Although no particular oven design is necessary in order to comply with the principles of the present invention, the oven (24) should include a heating unit (26) and a temperature sensor (28). In certain preferred embodiments, the heating unit (26) provides heat to the oven (24) in response to a control signal generated by the processing means (40). In order to ensure that the temperature within the oven (24) is at a desired level, the sensor (28) generates a feedback signal representative of the temperature in the oven (24), which signal is provided to the processing means (40). In certain preferred embodiments, an ambient temperature sensor (28b) and ambient pressure sensor (28c) each provides an ambient calibration signal to the processing means (40). The carrier gas/sample combination passing through the column (18) is exposed to a temperature profile resulting from the operation of the heater (26) within the oven (24). Typically, the temperature in the oven (24) is increased from a minimum level to a maximum level in a stepwise linear fashion. During this profile of changing—that is, rising or falling—temperatures, the sample (11) will separate into its components primarily due to differences in their partial pressures in the stationary phase versus the mobile phase.

As carrier gas containing the sample components exits the column (18), the presence of the components is detected by a detector (30). Those skilled in the art will appreciate that the detection of certain difficultly-detected components may be enhanced by derivatizing or otherwise chemically modifying the components prior to detection. For example, it is known to pass difficultly-detected components through devices such as nickel catalyst methanizers or fluorescence derivatizers to enhance their detection. It is intended that the term "detector" include such devices.

There exists a wide variety of useful chromatographic detectors, such as the flame ionization detector (FID), photoionization detector (PID), nitrogen phosphorous detector (NPD), flame photometric detector (FPD), thermal conductivity detector (TCD), atomic emission detector (AED), electrolytic conductivity detector (ELCD), and electron capture detector (ECD). Mass spectral detectors and infrared spectral detectors are also known. The detector (30) can be any of the GC detectors known in the art, so long as it is capable of determining at least one physicochemical property of the carrier fluid which exits the column (18). Typically, the detector (30) determines the magnitude of the physicochemical property. It is intended that the term "physicochemical property" include any physical and/or chemical property of a composition of matter.

It will be appreciated by those skilled in the art that the performance of many chromatographic detectors is dependent upon the physicochemical properties of the support fluid employed and that one or more detector response attribute such as sensitivity, selectivity, linear dynamic range, noninterference, activation, and robustness can be optimized by carefully modifying one or more physicochemical property of the carrier fluids and/or support fluids provided thereto. For example, by modifying one or more physicochemical property of the detector support gasses, one can optimize detector sensitivity in an FPD or FID, minimize quenching in an FPD, minimize solvent quenching of an NPD bead, or minimize lowered detector response with higher molecular weight compounds in a TCD. Where the devices of the prior art could only optimize for one set of flow rates and one chromatographic temperature, the present invention permits time-domain optimization of detector response.

Fluid physicochemical properties of interest in connection with the present invention include composition (e.g., elemental constitution), pressure, flow rate, viscosity, temperature, density, electronegativity, flammability, thermal conductivity, molecular weight, spectral emissions, and specific heat. Preferred fluid physicochemical properties include composition, pressure, and flow rate. It will be recognized that the term "composition" includes the findings of any qualitative and/or quantitative constitutional evaluation of the fluid, including elemental and molecular analyses, whether expressed relative or absolute terms.

Figure 2:
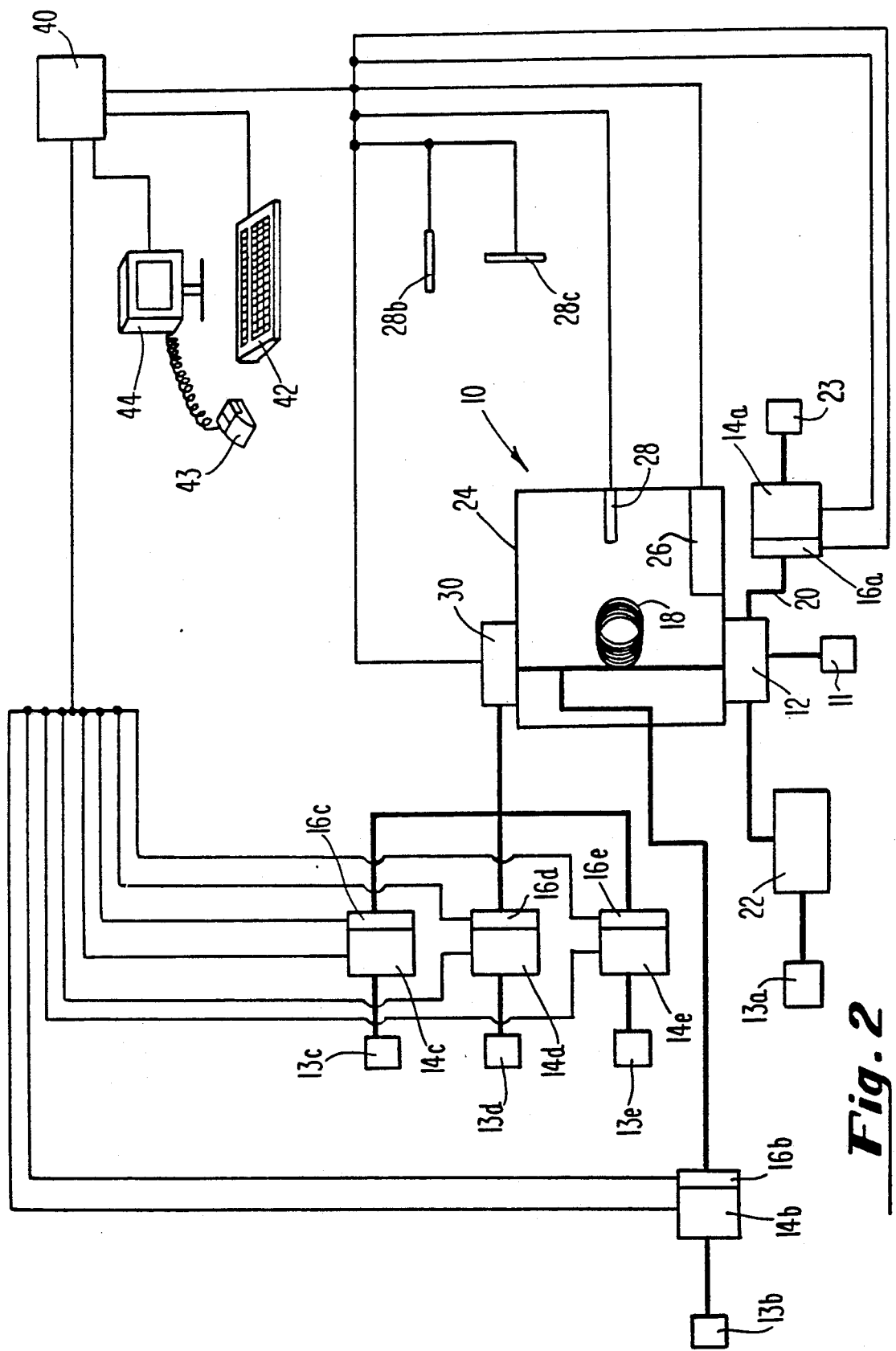
FIG. 2 is a block diagram of a back pressure regulated gas chromatographic apparatus according to the present invention.

The apparatus shown in FIG. 1 is said to be a forward pressure regulated gas chromatograph because the valve which regulates the pressure of the carrier gas in the region located forward from or downstream from the valve. Without departing from the principles of the present invention, the pressure of the carrier gas can also be regulated according to a back pressure mode, wherein the valve (14a) regulates pressure in the region located back from or upstream from the valve. For example, the chromatograph (10) depicted in FIG. 2 is arranged in a back pressure regulated design suitable for so-called split injections. In a split injection, a portion of the sample (11) to be analyzed is injected onto the column (18) while the remainder of the sample (11) is "split" off the column (18) and directed out the vent (23). Split injection techniques include so-called hot split, hot splitless, cold split and cold splitless injection techniques.

As depicted in FIG. 2, the carrier gas is provided directly to the injection port (12) from a mass flow controller (22). The pressure of the carrier gas is determined by the pressure transducer (16a) which senses the pressure of the carrier gas/sample combination in the non-analyzed output (20). The pressure of the carrier gas is controlled by a valve (14a) in response to an appropriate signal from processing means (40). The ratio between that portion of the sample/carrier gas provided to the output (20) and the remainder provided to the column (18) is known as the split ratio. The split ratio regulates the amount of the carrier gas/sample combination which passes through the column (18). The pressure of the carrier gas in the column (18) is controlled by operation of the valve (14a). As will be seen hereinafter, controlling the pressure of the carrier gas also controls its flow rate.

The chromatographic devices of the present invention preferably comprise means for providing gas to the chromatographic system at a point between the column (18) and the detector (30), as depicted in FIGS. 1 and 2. Such gas is provided in an amount sufficient to maintain a predetermined physicochemical property of the carrier fluid as it passes to the detector (30), preferably a constant, predetermined flow rate or pressure. For example, where the flow rate of carrier fluid exiting the column (18) decreases linearly from 20 to 10 ml/min over the course of a chromatographic run, the amount of fluid provided to the system between the column (18) and the detector (30) should increase linearly from 10 to 20 ml/min over the same interval. Those skilled in the art will recognize that the flow rate of the carrier gas might be determined by, for example a flow transducer placed between the column (18) and the detector (30). Alternatively, the flow rate may be calculated from the column temperature and the pressure determined by transducer (16a). Thus, the particular device or system employed to determine the flow or pressure provides one example of means for determining a physicochemical property of the carrier fluid at a point upstream from the detector.

In accordance with the present invention, the gas provided at a point between the column (18) and the detector (30) is known as make-up gas or, more generally, make-up fluid. The provision of an amount of make-up fluid sufficient to maintain a constant flow or pressure of carrier gas to the detector (30) provides a means for optimizing chromatographic performance by making it possible to program the flow rate or pressure of the carrier gas through the column (18) independent of concerns as to the flow rate or pressure of the carrier gas as it enters the detector (30).

It will be appreciated that the make-up gas may be the same as or different than the carrier gas and may comprise one or more component gasses depending upon the particular chromatographic separation to be performed. The means for providing make-up gas comprises a gas source (13b) which provides the make-up gas to a valve (14b). The valve (14b) serves to control both the pressure and the flow rate of the make-up gas provided to the GC system. A transducer (16b) generates an electronic signal in relation to the pressure or the flow rate of the make up gas. Preferably, a pressure signal is provided to a processing means (40), which in turn generates a control signal which it transmits to the valve (14b). The valve (14b) regulates the pressure of the make-up gas in response to a control signal.

Preferred chromatographic devices further comprise means for providing support gas to the detector (30). It will be appreciated that the support gas may comprise one or more component gasses—such as, for example, hydrogen, nitrogen, helium, air, or oxygen—depending upon the particular detector employed A preferred means for providing a support gas which comprises up to three different component gasses is shown in FIGS. 1 and 2 to comprise three gas sources (13c, 13d, 13e) which each provide a component gas to a valve (14c, 14d, 14e). The valves serve to control both the pressure and the flow rate of the support gas components. Transducers (16c, 16d, 16e) generate electronic signals in relation to the pressures or the flow rates of the component gases. Preferably, pressure signals are provided to a processing means (40), which in turn provides control signals to the valves (14c, 14d, 14e). The valves regulate the pressure of the component gases in response to control signals. Hence, the valves also regulate the pressure of the support gas. It will be recognized that where a support gas comprises more than three component gases, the system of gas sources, valves, and transducers shown in FIGS. 1 and 2 may be expanded as necessary. It will also be recognized that where the detector employs a flame, the components of the support gas usually will only be mixed at or near the flame location.

In accordance with the present invention, the processing means (40) operates the devices depicted in FIGS. 1 and 2. It will be recognized, however, that the present invention is an advance over other GC systems because the detection of sample components during an analysis has been directly related to the physicochemical properties of the carrier fluids and/or the support fluids Such regulation is achieved primarily by the processing means (40), which maintains overall control of all systems associated with the gas chromatograph.

Processing means (40) amenable to the practice of this invention consist of one or more computing devices such computers, microprocessors, microcontrollers, capacitors, switches, logic gates, or any equivalent logic device capable of compiling and executing instructions. Processing means (40) preferably are coupled with a data input means such as a keyboard (42), keypad, or computer mouse (43) and a data output means such as a video display (44) or printer. Preferred processing means (40) further include devices capable of generating control signals in response to input data, as well as devices in which information and programming can be stored and retrieved. The processing means (40) may further comprise input/output isolation devices, clocks and other related electronic components. The processing means (40) preferably also comprises an operating system or programming environment for the generation of source code in an appropriate programming language, along with a compiler or other means of converting such source code into executable programs. A preferred processing means is the Z80 microprocessor from the Zilog Company of Cupertino, CA. Another useful processing means is a personal computer such as a Hewlett-Packard Vectra 386/25 in networked dialogue with the Z80 microprocessor.

One function of the processing means (40) is to control the operation of the valves (14a–e) and, hence, both the pressure and flow rate of the carrier fluid and/or support fluid. The processing means (40) controls the valves (14a–e) by transmitting to each valve a control signal which causes the valve to increase or decrease the pressure or flow rate of the fluid passing therethrough. In preferred embodiments, the pressure transducers (16a–e) sense the pressure of the gas and transmit to the processing means (40) pressure feedback signals representative of such pressure By monitoring the pressure feedback signals from the pressure transducers (16a–e), the processing means (40) can maintain the pressure at some desired level by generating control signals directing the operation of the valves (14a–e). Since the generated control signals are in a digital form, they preferably are converted to analog form by a digital to analog converter and appropriately amplified by an amplifier prior to transmission to valves (14a–e). The gas pressures as sensed by the transducers (16a–e) preferably are provided to the processing means (40) by first converting the analog signals generated by the pressure transducers (16a–e) from analog to a digital signal by a converter. The digital signals generated by the converter are supplied to the processing means (40).

Operating commands and other information necessary to perform a chromatographic analysis are entered into the processing means (40) by way of the input means (42 or 43). For example, known physicochemical properties of the particular fluids employed may be entered in this manner, as may detector response attributes and column temperature programs. Messages prompting the user to enter certain information can be generated by the processing means (40) and displayed on the output means (44).

Another function of the processing means (40) is to control the temperature of the oven (24). The processing means (40) controls oven temperature by transmitting to the heater (26) a control signal which causes the heater to increase or decrease the amount of heat transferred to the oven (24). The sensor (28) senses the temperature in the oven (24) and transmits a feedback signal representative of such temperature to the processing means (40). By monitoring the temperature feedback signal from the sensor (28), the processing means (40) can maintain the temperature in the oven (24) at some desired level by controlling the heater (26).

Figure 3:
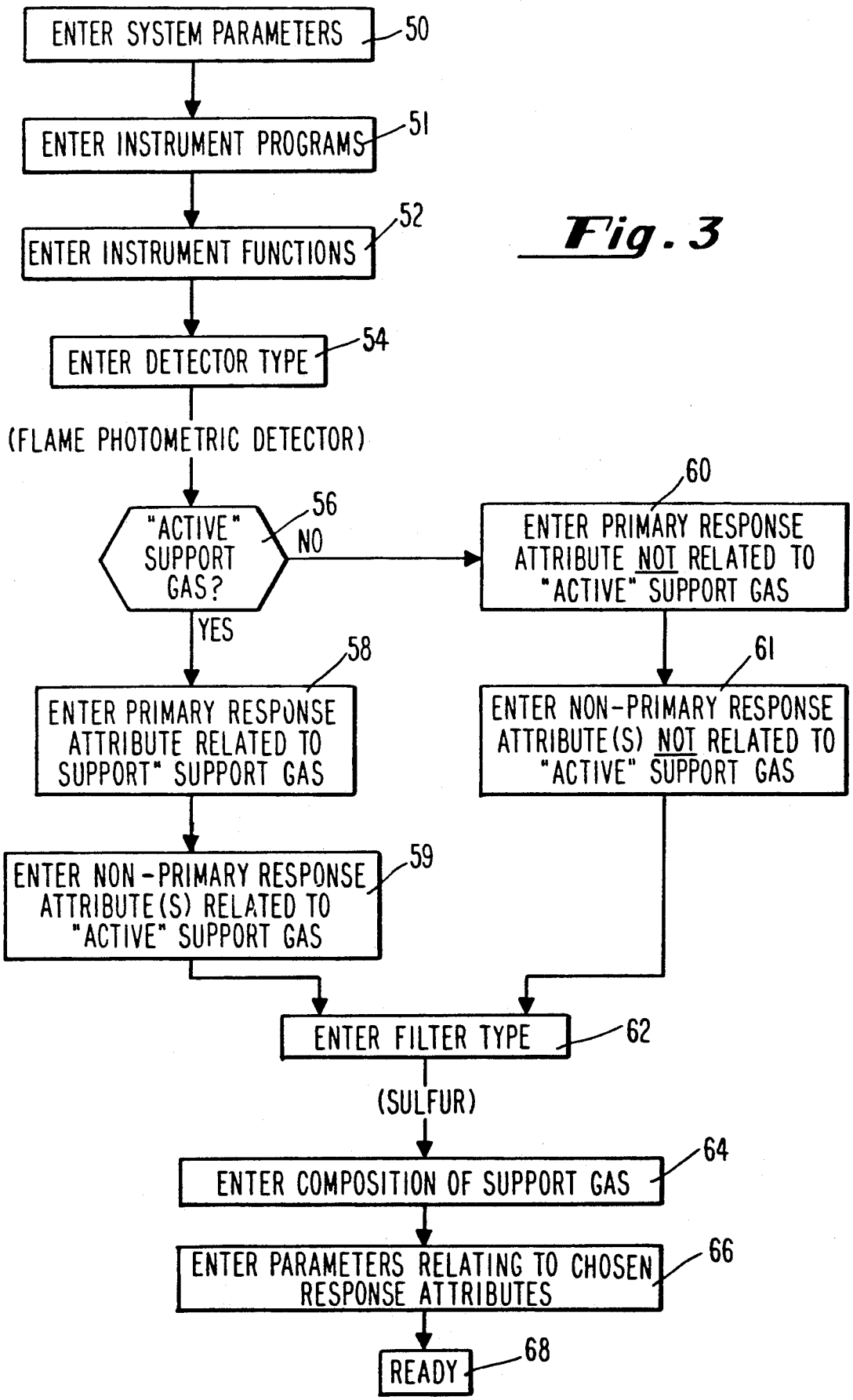
FIG. 3 is a flow chart of a preferred procedure for programming an apparatus according to the present invention prior to a chromatographic analysis.
Figure 4:
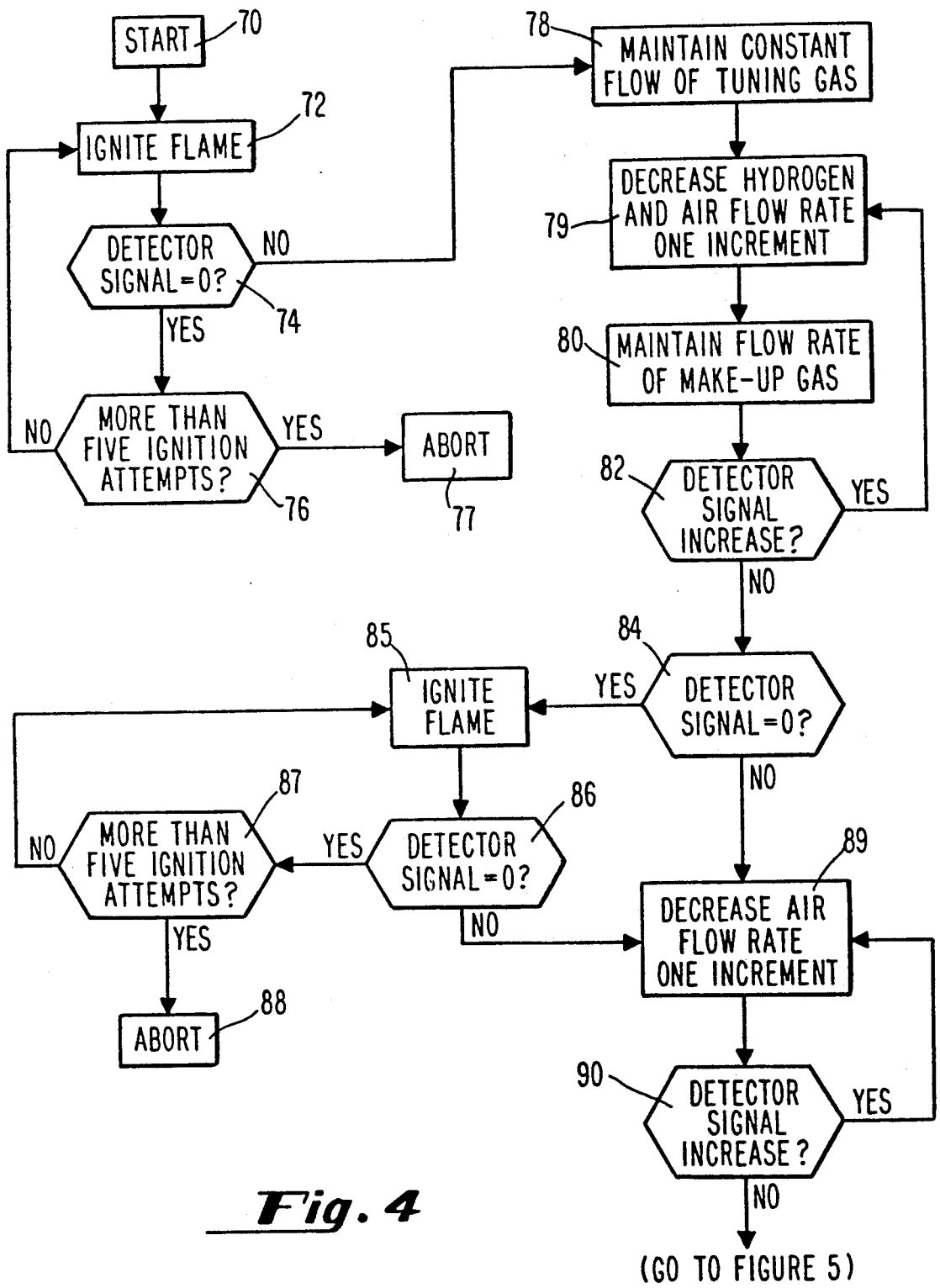
FIGS. 4 and 5 are flow charts of the operations performed by an apparatus according to the present invention in optimizing the sensitivity of a flame photometric detector.
Figure 5:
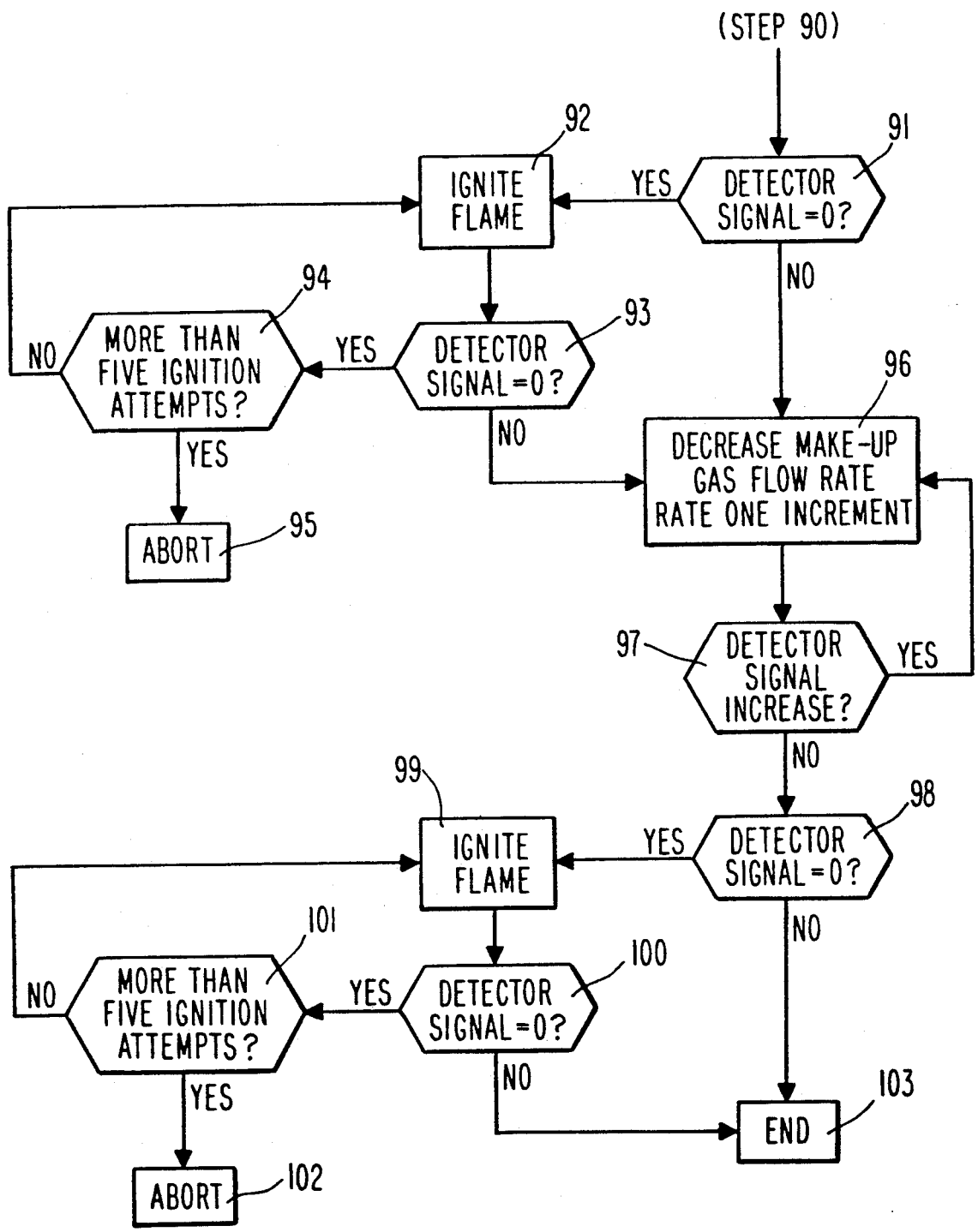

Turning to FIGS. 3 and 4, the present invention will be described by reference to a preferred embodiment. It should be understood that where input is to be supplied to a program or sub-program said input can be provided in interactive mode by an operator or can be taken directly from a file containing the pertinent information. Generally, the processing means (40) stores the entered information into its memory for later retrieval. As will become apparent, certain of the information stored in the memory will be stored in a time sequential format.

FIG. 3 shows a preferred, general process by which a user prepares a device such as depicted in FIG. 1 for a chromatographic analysis The user at step 50 enters system parameters such as temperature, flow, pressure setpoints, assignment of signals and range/attenuation, autosample parameters, valve timed events, and detector mode (i.e., FPD-sulfur mode with hydrogen/nitrogen/air). At step 51, the user enters instrument programs such as the programs relating to modification during the chromatographic run of column pressure, column flow, or oven temperature. At step 52, the user enters instrument functions such as whether or not make-up gas is to be provided. In a chromatographic system using high resolution (low flow) capillary columns, it is preferred that make-up fluid be provided. It is preferred that the make-up fluid have the same composition as the carrier fluid. Thus, it will be appreciated that the make-up fluid may be provided either from gas source (13a) or (13b). The system parameters, programs, and functions are entered as appropriate for the particular chromatographic run to be performed.

At step 54, the user enters the type of detector to be employed. The user then determines at step 56 which detector support gases will be used to support the flame or chemical reaction. If the detector (30) does employ such support gases, the user at step 58 identifies a primary response attribute relating to detectors which employ "active" support gasses such as, for example, flame robustness, non-interference, sensitivity, linearity, selectivity, and constant response factor. It will be recognized that constant response factor relates to maintaining the same relative signal per unit mass or volume for each analyte. The user identifies the primary detector response attribute—that is, the response attribute whose optimization is of greatest experimental importance to the user—by entering it via the input means. Thus, preferred means for identifying detector response attributes comprise input means. A hierarchy of response attributes for optimization may be established by entering at step 59 one or more response attributes of lesser importance.

If the detector (30) does not employ an "active" support gas, the user identifies at step 60 a primary detector response attribute such as, for example, sensitivity, linearity, and constant response factor. At step 61, the user may establish a hierarchy of response attributes by entering one or more response attributes of lesser importance.

Where the flame photometric detector is chosen, the user selects at step 62 whether a phosphorous or sulfur filter is being employed.

At step 64, the user enters the chemical composition of the support gas. Alternatively, the chromatographic apparatus may further comprise means for automatically determining the composition of the support gas. Thus, both the input means and the means for automatically determining the composition of the support gas provides examples of means for determining a physicochemical property of the support gas.

Where a sulfur filter is chosen for an FPD, a possible support gas would be one of air, hydrogen gas, and hydrogen sulfide gas. Accordingly, the gas sources (13c, 13d, and 13e) should contain air, hydrogen gas, and hydrogen sulfide gas, respectively It will be appreciated that the composition of the support gas may vary from one chromatographic run to another and will be dependent upon a wide variety of factors, such as the detector (30) employed, the response attribute to be optimized, the chromatographic column (18), and the temperature, pressure, flow rate and composition of the carrier gas provided to the detector (30).

The user next inputs information relating to the primary detector response attribute identified at step 58. For example, if sensitivity were identified as the primary detector response attribute, the user preferably enters at step 66 parameters relating to optimizing the sensitivity of the detector (30). Preferred parameters relating to sensitivity include the initial flow rate of the hydrogen gas, the increment by which the hydrogen flow rate will increase during optimization, the ratio of air to hydrogen, the increment by which the air to hydrogen will increase during optimization, the flow rate of make-up gas in relation to the flow rate of the carrier gas exiting the column (18), and increment by which the flow rate of the make-up gas will increase during optimization. Having received the above-entered information, the processing means (40) gives an indication at step 68 that it is ready to begin a chromatographic analysis run.

Turning now to FIG. 4, tuning of the chromatographic apparatus will be described. The procedure is started at step 70. This start can either be achieved by an indication from the processing means (40) that all system and flow information has been gathered or can be achieved by the user entering an appropriate command on the keyboard (42). At step 72, the processing (40) means transmits a control signal to the detector (30) to ignite the FPD flame. The detector (30), in turn, provides a detector signal to the processing means (40). At step 74, the processing means (40) determines whether the detector signal is equal to zero. If the detector signal is zero, the processing means (40) determines at step 76 whether more than five unsuccessful attempts have been made to ignite the flame. If five or fewer such attempts have been made, flame ignition is again performed at step 72. The run is aborted where more than five unsuccessful lighting attempts are made.

Where the detector signal is not zero, the processing means (40) at step 78 preferably sends a control signal to valve (14e) to provide a predetermined concentration of a sulfur-containing tuning gas such as hydrogen sulfide.

At step 79, the processing means (40) starts the primary tuning sequence by sending control signals to valves (14c and 14d), decreasing the flow rate of hydrogen and air by one incremental amount while maintaining the air/hydrogen ratio. A control signal is also sent at step 80 to valve (14b) to maintain the flow rate of the make-up gas. The detector (30) next transmits a detector signal to the processing means (40), which at step 82 compares the signal with the detector signal evaluated at step 74. If the detector signal has increased, steps 79 and 80 are repeated; that is, the flow rates of hydrogen and air are modified in relation to the control signal. Where steps 79 and 80 are repeated, the valve (14b) provides an example of means for modifying a physicochemical property of the support gas in relation to the control signal.

Where the performance of steps 79 and 80 do not increase the detector signal, the processing means (40) at step 84 determines whether the last provided detector signal is equal to zero. At this point in a chromatographic run, it will be appreciated that a detector signal of zero will most likely be provided where the detector flame has accidentally been extinguished or "flamed out". If the signal is not zero, the processing means (40) proceeds to step 89. If the signal is zero, the processing means (40) at step 85 transmits a control signal to the detector (30) to ignite the flame. The detector (30) again provides a detector signal to the processing means (40), which determines at step 86 whether the signal is equal to zero. If the signal is not equal to zero, the processing means (40) proceed to step 89. If the signal is equal to zero, the processing means (40) at step 87 determines whether more than five unsuccessful attempts to light the flame have been made. If so, the run is aborted at step 88; if not, the processing means (40) proceeds to step 92 and attempts to re-ignite the flame.

At step 89, the processing means (40) begins its secondary tuning procedure by reducing the air/hydrogen ratio by the increment selected at step 66. The detector (30) then sends a detector signal to the processing means (40), which at step 90 compares it with the detector signal evaluated at step 84 or 86. If the signal is greater than the signal evaluated at step 84 or 86, step 89 is repeated. If the signal is not greater, the processing means (40) at step 91 determines whether the last provided detector signal is equal to zero, that is, if flame-out has occurred. If the signal is not zero, the processing means (40) proceeds to step 96. If the signal is equal to zero, the processing means (40) at step 92 transmits a control signal to the detector (30) to ignite the flame. The detector (30) again provides a detector signal to the processing means (40), which determines at step 93 whether the signal is equal to zero. If the signal is not equal to zero, the processing means (40) proceeds to step 96. If the signal is equal to zero, the processing means (40) at step 94 determines whether more than five unsuccessful attempts to light the flame have been made. If so, the run is aborted at step 95; if not, the processing means (40) proceeds to step 92 and attempts to re-ignite the flame.

At step 96, the processing means (40) begins its tertiary tuning procedure by reducing the flow rate of the make-up gas by the increment selected at step 66. The detector (30) then sends a detector signal to the processing means (40), which at step 97 compares it with the detector signal evaluated at step 91 or 93. If the signal is greater than the signal of step 91 or 93 step 96 is repeated. If the signal is not greater, the processing means (40) at step 98 determines whether the last provided detector signal is equal to zero, that is, if flame-out has occurred. If the signal is not equal to zero, the processing means (40) proceeds to step 103, ending optimization for detector sensitivity. At this point, valve (14e) is closed, shutting off the supply of sulfur-containing tuning gas. If the signal is equal to zero, the processing means (40) at step 99 transmits a control signal to the detector (30) to ignite the flame. The detector (30) again provides a detector signal to the processing means (40), which determines at step 100 whether the signal is equal to zero. If the signal is not equal to zero, the processing means (40) proceeds to step 103, ending optimization for detector sensitivity. If the signal is equal to zero, the processing means (40) at step 101 determines whether more than five unsuccessful attempts to light the flame have been made. If so, the run is aborted at step 102; if not, the processing means (40) proceeds to step 99 and attempts to re-ignite the flame.

While the foregoing example primarily concerns optimizing the sensitivity of an FPD by adjusting certain selected physicochemical properties of the support fluid and the carrier fluid, it will be appreciated by those skilled in the art that the apparatus and methods of the present invention may be applied to optimize virtually any response attribute for the full range of known chromatographic detectors, and that the physicochemical properties to be adjusted in achieving such optimal conditions will vary with the particular chromatographic separations which might be performed. Detector response attributes whose optimization is preferred in accordance with the present invention include sensitivity, selectivity, linear dynamic range, activation, robustness, and noninterference.

As employed herein, the term "sensitivity" is intended to relate to the amount of analyte that can be reliably discerned from background. It is often expressed as minimum detectable level (MDL), which is defined as a sample peak height multiplied by twice the background noise level. For example, it is known that the sensitivity of a flame photometric detector (FPD) is dependent upon both the flow rate and composition of its support gasses. By programming the flow rate of these support gasses in accordance with the present invention, it is possible to optimize detector sensitivity during a chromatographic run.

The terms "specificity" and "selectivity" are intended to be interchangeable and to relate to the capacity of a detector to determine the presence of a specific chemical moiety of interest. For example, the FPD is highly specific to certain classes of compounds, such as sulfur-or phosphorous-containing compounds. Specificity for an FPD typically is defined as the ratio of sulfur to carbon, sulfur to phosphorous, or phosphorous to carbon that gives the same response.

The term "linear dynamic range" is intended to relate to the linearity of increasing detector response versus increasing concentration of the sample compound. For example, an electron capture detector is known to be sensitive to halogenated compounds. Unfortunately, it does not always have the same degree of linearity for different compounds. In general, highly electron capturing compounds—such as those with multiple chlorine atoms—have different linearity curves than less strongly electron capturing compounds. These linearity curves can be somewhat modified by changing the flow rate of the make-up gas and, hence, resultant residence time in the detector cell.

The term "activation" is intended to relate to establishing a detector in its operative state. In the case of a detector such as an FID or FPD, activation relates to ignition of the detector flame. Helium is commonly used as a carrier gas and a make-up gas in conjunction with an FID. In many gas chromatographs, such as the Hewlett-Packard model 5890A device, the FID is ignited with a glow plug simultaneously with a drop in the flow rate of air to the detector to provide a rich hydrogen/oxygen mixture above the FID jet. However, when high helium flow rates are used, the helium is able to suppress the glow plug temperatures enough that it is very difficult to ignite the flame. With the FPD, the problem is that flow rates of both hydrogen and oxygen support gasses typically are relatively high. Thus, the FPD operates with a hydrogen-rich flame, resulting in a very explosive ignition when the glow plug is ignited. With programming control of FID make-up gas, however, it is possible to temporarily reduce the make-up flow rate during the ignition period. With instrumental control of the composition of the make-up gas, this can all be done automatically as part of an automated FID ignition sequence. And with programmable control the flow rate of hydrogen in a FPD, it is possible to provide a lean hydrogen mixture at ignition, resulting in nearly inaudible ignitions. This would also reduce the chance of hardware failure caused by explosive ignitions.

The term "robustness" is intended to relate to the capacity of the detector to provide a continuous detector signal over a long period of time. Thus, it will be appreciated that detector robustness relates to preventing any loss of sensitivity as well as to preventing flame termination. Flame robustness can be defined as ability to stay lit with normal detector response under a wide range of conditions. For example, it is difficult for the FID to remain lit when large volumes of difficultly combusted solvents are injected. When these solvents do burn, they tend do so with a great deal of soot which builds up in the FID and electrically shorts out the detector. Unfortunately, the conditions that minimize flame out or detector shorting also result in reduced detector sensitivity and relatively high consumption of detector gases. These problems can be eliminated with programmable support gas flow rates, such that the flow rates of air and hydrogen are elevated during the period that solvent elutes from the column (18), and can be reduced during the later period when trace level solutes elute.

The term "noninterference" is intended to relate to detector response when analytes of interest co-elute with other matrix components. In general, such interference is caused by a temporary disruption of detector reaction mechanisms. For example, in an FPD, if a sulfur-containing compound co-elutes with a hydrocarbon, the reaction leading to emission of photons can be impaired, momentarily "quenching" or interfering with response.

It may also be possible to optimize or extend the life of a detector in accordance with the present invention. For example, it may be possible to extend the life of an NPD bead or maintain the NPD bead in a "ready" condition while the detector is not actually in use. This can be done, in part, by flow diversion of solvent from the bead using a combination of programmable support gas flows and actuation of a venting flow path. This prevents solvents from chemically attacking the bead material.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for performing a chromatographic separation of a compound wherein a carrier fluid comprising said compound is passed through a column to a detector, comprising the steps of:
   determining a physicochemical property of the carrier fluid at the detector;
   generating a control signal in relation to the physicochemical property of the carrier fluid; and
   providing an amount of make-up fluid to the chromatographic system at a point between the column and the detector in relation to the control signal such that the carrier fluid passes to the detector with a predetermined physicochemical property.

2. The method of claim 1 wherein the carrier fluid and the make-up fluid are gases.

3. The method of claim 1 wherein the physicochemical property of the carrier fluid is selected from the group consisting of flow rate and pressure.

4. The method of claim 1 wherein the make-up fluid is provided to the chromatographic system such that the carrier fluid passes to the detector with a predetermined flow rate.

5. The method of claim 1 wherein the make-up fluid is provided to the chromatographic system such that the carrier fluid passes to the detector with a predetermined pressure.

6. A method for controlling the operation of a detector in a chromatographic system comprising a first source of support fluid and a second source of carrier fluid wherein at least one support fluid is passed from said first source to the detector, comprising the steps of:
identifying at least one detector response attribute;
determining at least one physicochemical property of the support fluid;
providing to a processing means a data set which comprises:
the detector response attribute; and
the physicochemical property;
generating a control signal in relation to the data set; and
modifying the physicochemical property in relation to control signal.

7. The method of claim 6 wherein the support fluid comprises a gas.

8. The method of claim 6 wherein the detector response attribute is selected from the group consisting of sensitivity, selectivity, linear dynamic range, noninterference, activation, and robustness.

9. The method of claim 6 wherein the physicochemical property of the support fluid is selected from the group consisting of composition, pressure, flow rate, viscosity, temperature, density, electronegativity, flammability, thermal conductivity, molecular weight, spectral emissions, and specific heat.

10. The method of claim 6 wherein the physicochemical property of the support fluid is selected from the group consisting of composition, pressure, and flow rate.

11. A method for controlling the operation of a detector in a chromatographic system comprising a first source of support fluid and a second source of carrier fluid wherein a support fluid is passed from said first source to the detector and a carrier fluid is passed from said second source through a column to the detector, comprising the steps of:
identifying at least one detector response attribute selected from the group consisting of sensitivity, selectivity, linear dynamic range, noninterference, activation, and robustness;
determining at least one physicochemical property of the support fluid selected from the group consisting of composition, pressure, flow rate, viscosity, temperature, density, electronegativity, flammability, thermal conductivity, molecular weight, spectral emissions, and specific heat;
determining at least one physicochemical property of the carrier fluid selected from the group consisting of composition, pressure, flow rate, viscosity, temperature, density, electronegativity, flammability, thermal conductivity, molecular weight, spectral emissions, and specific heat;
providing to a processing means a data set which comprises:
the detector response attribute;
the physicochemical property of the support fluid; and
the physicochemical property of the carrier fluid;
generating a control signal in relation to the data set; and
modifying a physicochemical property of the support fluid or the carrier fluid in relation to the control signal.

12. An apparatus for performing a chromatographic separation of a compound wherein a carrier fluid comprising said compound is passed through a column, comprising:
a detector in fluid communication with the column, comprising means for determining a physicochemical property of the carrier fluid;
means for generating a control signal in relation to the physicochemical property of the carrier fluid; and
means for providing an amount of make-up fluid to the chromatographic system at a point between the column and the detector in relation to the control signal such that the carrier fluid passes to the detector with a predetermined physicochemical property.

13. The apparatus of claim 12 wherein the carrier fluid and the make-up fluid are gases.

14. The apparatus of claim 12 wherein the means for determining a physicochemical property of the carrier fluid comprises a device selected from the group consisting of pressure transducers and flow transducers.

15. The apparatus of claim 12 wherein the physicochemical property is selected from the group consisting of flow rate and pressure.

16. An apparatus for controlling the operation of a detector in a chromatographic system comprising a first source of support fluid and a second source of carrier fluid wherein at least one support fluid is passed from said first source to the detector, comprising:
means for identifying at least one detector response attribute;
means for determining at least one physicochemical property of the support fluid;
processing means for generating a control signal in relation to a data set which comprises:
the detector response attribute; and
the physicochemical property; and
means for modifying the physicochemical property in relation to the control signal.

17. The apparatus of claim 16 wherein the support fluid comprises a gas.

18. The apparatus of claim 16 wherein the detector is selected from the group consisting of flame ionization detectors, photoionization detectors, nitrogen phosphorous detectors, flame photometric detectors, thermal conductivity detectors, atomic emission detectors, mass spectral detectors, infrared spectral detectors, electrolytic conductivity detectors, and electron capture detectors.

19. The apparatus of claim 16 wherein the detector response attribute is selected from the group consisting of
sensitivity, selectivity, linear dynamic range, noninterference, activation, and robustness.

20. The apparatus of claim 16 wherein the physicochemical property of the support fluid is selected from the group consisting of composition, pressure, flow rate, viscosity, temperature, density, electronegativity, flammability, thermal conductivity, molecular weight, spectral emissions, and specific heat.

21. The apparatus of claim 16 wherein the physicochemical property of the support fluid is selected from the group consisting of composition, pressure, and flow rate.

22. The apparatus of claim 16 wherein the means for determining at least one physicochemical property of the support fluid comprises a device selected from the group consisting of pressure transducers and flow transducers.

23. The apparatus of claim 16 wherein the means for modifying the physicochemical property comprises a valve.

24. An apparatus for controlling the operation of a detector in a chromatographic system comprising a first source of support fluid and a second source of carrier fluid wherein a support fluid is passed from said first source to the detector and a carrier fluid is passed from said second source through a column to the detector, comprising:
  means for identifying at least one detector response attribute selected from the group consisting of sensitivity, selectivity, linear dynamic range, non-interference, activation, and robustness;
  means for determining at least one physicochemical property of the support fluid selected from the group consisting of composition, pressure, flow rate, viscosity, temperature, density, electronegativity, flammability, thermal conductivity, molecular weight, spectral emissions, and specific heat;
  means for determining at least one physicochemical property of the carrier fluid selected from the group consisting of pressure, flow rate, composition, viscosity, temperature, density, electronegativity, flammability, and thermal conductivity; processing means for generating a control signal in relation to a data set which comprises:
  the detector response attribute;
  the physicochemical property of the support fluid; and
  the physicochemical property of the carrier fluid; and
  means for modifying a physicochemical property of the support fluid or the carrier fluid in relation to the control signal.

* * * * *